United States Patent [19]

Seager

[11] 4,151,458
[45] Apr. 24, 1979

[54] CLOSELY SPACED PIPE-TO-SOIL ELECTRICAL SURVEY METHOD AND APPARATUS

[75] Inventor: William H. Seager, Edmonton, Canada

[73] Assignee: Harco Corporation, Medina, Ohio

[21] Appl. No.: 820,379

[22] Filed: Jul. 29, 1977

[51] Int. Cl.² .................. G01V 3/00; G01R 31/02
[52] U.S. Cl. .................. 324/9; 324/71 R; 324/72
[58] Field of Search ............ 324/1, 3, 9, 67, 54, 324/52, 71 R, 65 P, 65 CR, 72

[56] References Cited

U.S. PATENT DOCUMENTS

| | | | |
|---|---|---|---|
| 2,105,247 | 1/1938 | Jakosky | 324/1 |
| 2,167,490 | 7/1939 | Ryan | 324/67 |
| 2,256,742 | 9/1941 | Jakosky | 324/9 X |
| 2,378,440 | 6/1945 | Scott | 324/9 X |
| 2,744,232 | 5/1956 | Shawhan et al. | 324/3 |
| 2,775,736 | 12/1956 | Pies et al. | 324/67 X |
| 2,974,276 | 3/1961 | Davis | 324/9 X |
| 2,988,691 | 6/1961 | McAlister et al. | 324/1 |
| 3,735,249 | 5/1973 | Stoll | 324/9 |
| 4,063,161 | 12/1977 | Pardis | 324/9 X |

Primary Examiner—Gerard R. Strecker
Attorney, Agent, or Firm—Maky, Renner, Otto & Boisselle

[57] ABSTRACT

A method and apparatus for making relatively closely spaced pipe-to-soil potential difference measurements, the method and apparatus being characterized by a dual function economically disposable, relatively lightweight, flexible electrical wire that provides for the necessary electrical connection to a pipeline and also for accurate distance measurement at the test end of the wire along the pipeline. The wire is electrically connected at a test station or lead to the pipeline and is played out from a supply thereof carried by the surveyor along the length of the pipeline through distance measuring means. At each selected test location, the potential between the wire connected to the pipe and a reference electrode contacting the soil proximate the pipe are measured by a high resistance input meter. The wire is economically disposable and may be discarded when no longer used eliminating the need to rewind the wire.

24 Claims, 5 Drawing Figures

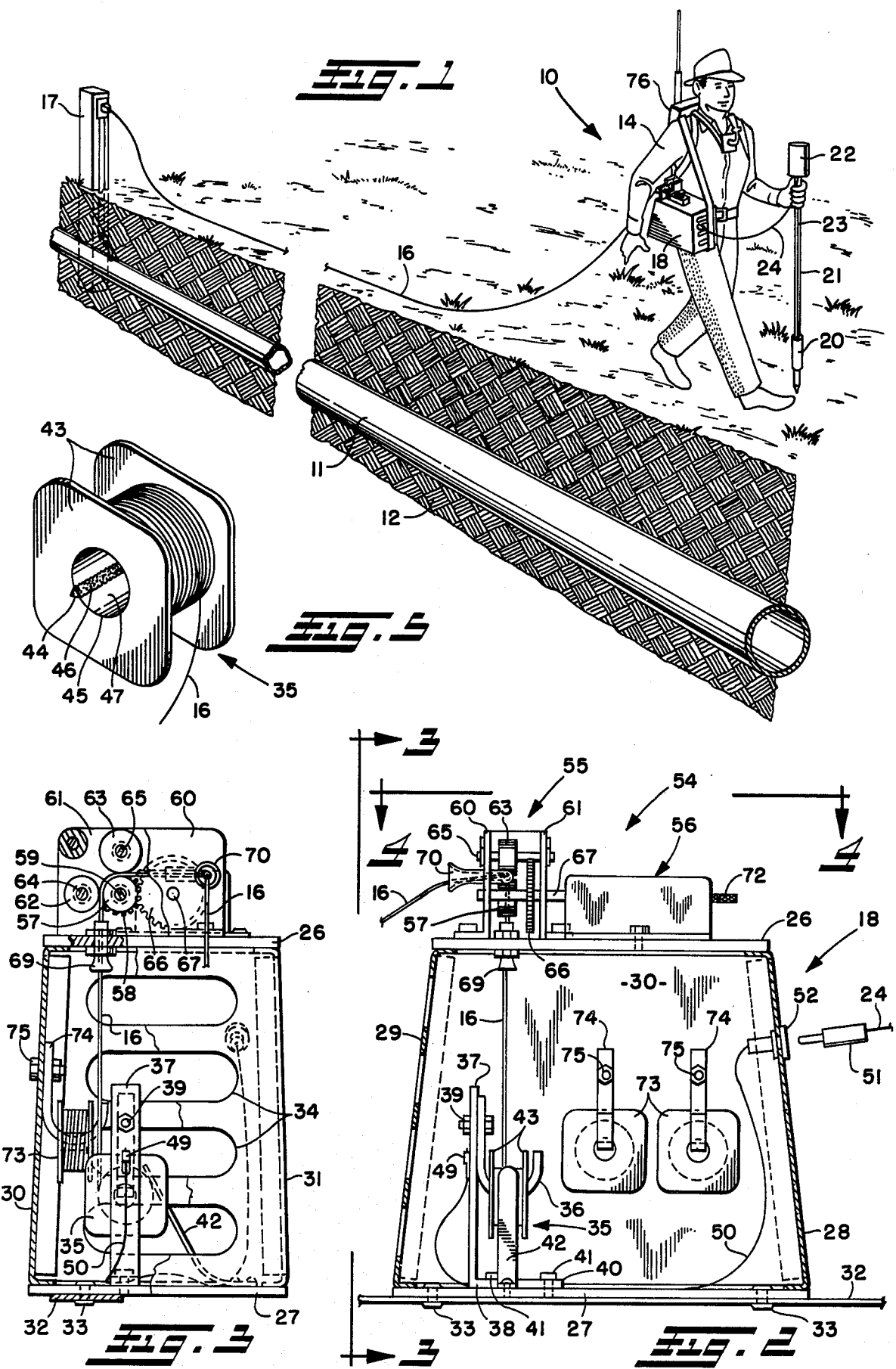

CLOSELY SPACED PIPE-TO-SOIL ELECTRICAL SURVEY METHOD AND APPARATUS

BACKGROUND OF THE INVENTION

The present invention relates generally as indicated to pipe-to-soil potential difference surveys, and more particularly to a method and apparatus for making closely spaced pipe-to-soil potential surveys.

In controlling corrosion of pipelines or other elongate structures buried in the ground, an electrical potential is applied to the pipeline to reduce the potential difference to a minimum negative potential difference between the pipe and adjacent soil or water. To determine where the voltage should be applied and to assure that sufficient voltage is applied to the pipeline, electrical measurements are made to determine the pipe-to-soil difference along the length of the pipeline. The electrical potential is applied by conventional cathodic protection devices.

Such electrical measurement requires a contact to the pipe, a suitable voltmeter or potentiometer, a means of contacting the ground and connecting wires. A copper-copper sulfate ($Cu-CuSO_4$) cell is an industry standard for providing the necessary contact with the ground.

Measurements are commonly made on a yearly interval basis at test lead stations. Test leads are wires connected to the underground pipe brought above ground and permanently mounted in a device to protect the wire and allow easy accessibility. Test leads are installed at locations along the pipe, usually spaced one to two miles apart.

In addition to this type of survey, which provides pipe-to-soil potential measurements at test lead locations only, a continuous, over the pipeline, closely-spaced survey is conducted occasionally to determine the pipe-to-soil potential difference measurements at intervals of, for example 10 to 25 feet along the length of the pipe.

Heretofore, a reel of relatively heavy insulated wire has been connected to the pipe at a reference location, preferably a test lead. The insulated wire would then be dragged from the reel across the ground along the route of the pipe and the copper-copper sulfate half cell would be placed directly over the pipe at intervals of 10 to 25 feet or whatever spacing desired. Distance from the test lead would be determined by chaining, or by measuring with a wire measuring device mounted at the reel at the reference location. The voltage measurement between the wire (connected to the pipe via the reel and test station) and the copper-copper sulfate half cell would then be made with a suitable voltmeter or potentiometer at the spaced intervals. Radio contact would be maintained between the man at the reel location, and the men at the end dragging the wire. This was necessary for distance determination and recording of the readings observed at the voltmeter located at the half cell location. When the next test lead would be reached (usually within 8,000 feet), the half cell would be disconnected, and the wire would be reeled back (usually by electric power) and transported to the next test lead location along the pipeline surveyed.

This system, however, has a number of disadvantages, namely the wire and reel and power re-winding mechanism are heavy and require truck or van transport. The reel itself may weigh on the order of 300 lbs. At most of the surveys are done over farm land, crops, etc., the use of a vehicle is generally prohibited, and the pipeline owner usually specifies that only walking over the right of way be allowed. Furthermore, the effort required to drag the wire is considerable often requiring several men, especially when trying manually to pull a mile of wire across uneven terrain. Moreover, the resultant wear on the wire and frequent breakage, plus electric reel maintenance, further add to the cost of this system.

SUMMARY OF THE INVENTION

The closely spaced survey method and apparatus of the present invention provides for equally reliable surveys in a much more simplified manner. Moreover, it is possible to survey substantially greater distances in equal time at substantially less cost.

The survey method of the present invention contemplates a dual function of economically disposable, relatively lightweight, flexible wire providing for the necessary electrical connection to the pipe and for accurate distance measurement along the length of the pipe. The wire wound on a reel is electrically and mechanically connected to the pipeline at a test lead station. Because of its light weight, the wire and reel may be carried by a surveyor and played out behind him as he traverses the length of the pipe. As the wire is played out, it drives a distance measuring unit carried by the surveyor for measuring the distance from the test station and between each test location. At each test location, the surveyor contacts the copper-copper sulfate half cell or the like to the ground above the pipe and the potential measurement between the wire and the half cell is made with a suitable meter also carried along with the surveyor. A single surveyor thus makes both the distance and potential measurements. The surveyor may record the measurements in a notebook, record them on a portable tape recorder, for example, or transmit them by radio for recording at a different location. Hence there is no longer any need for a man to be positioned at the test lead attachment at the starting point of the survey to make distance measurements and correlate such measurements with the potential measurements of the surveyor. In addition, wire is no longer dragged over the ground but is merely layed down. The wire is economically disposable and may never be reeled back for re-use.

The apparatus for conducting the closely-spaced survey comprises a copper-copper sulfate half cell or similar reference electrode carried on the lower end of a cane which may be brought into contact with the soil proximate the pipeline at the various test points. Economically disposable, relatively lightweight, flexible electrical wire and spool are mounted in a distance measuring unit carried by the surveyor, the wire having one end adapted for electrical connection at the test lead to the pipe. The distance measuring unit is driven by the wire as it is played out along the pipe, whereby accurate distance measurements may be obtained at the surveyor's or test end of the wire. If the voltmeter were back at the reel, 100% wire insulation would be a vital necessity; however, with the meter at the cell end, insulation is not nearly as critical. The spool and wire are electrically connected to a suitable meter provided on top of the cane for measuring the potential between the reference electrode and the wire or pipe at the various test locations.

It is accordingly a principal object of this invention to provide a more efficient and inexpensive method and apparatus for conducting a closely spaced pipeline electrical survey.

Another principal object is the provision of such survey method and apparatus utilizing a lightweight, economically disposable wire which need not be re-reeled.

A further important object is the provision of such survey method and apparatus in which the wire may drive a distance measuring device carried by the surveyor.

Still another important object is the provision of an electrical pipeline survey in which a single person walking or traversing the pipeline may make and record both distance and potential measurements.

Another object is the provision of compact and portable apparatus for making such survey which can be readily carried by a single person.

Other objects and advantages will appear from the ensuring specification.

To the accomplishment of the foregoing and related ends the invention, then, comprises the features hereinafter fully described and particularly pointed out in the claims, the following description and the annexed drawings setting forth in detail certain illustrative embodiments of the invention, these being indicative, however, of but a few of the various ways in which the principles of the invention may be employed.

BRIEF DESCRIPTION OF THE DRAWINGS

In the annexed drawings:

FIG. 1 is a broken perspective view illustrated of the survey method of the present invention and the apparatus for practicing the same;

FIG. 2 is a fragmentary longitudinal section through the distance measuring unit of the apparatus;

FIG. 3 is an end view partly broken away and in section of the unit of FIG. 2, as seen from the plane of the line 3—3 thereof;

FIG. 5 is an enlarged perspective view of the wire and spool illustrating the soldered connection between the same.

DESCRIPTION OF THE PREFERRED EMBODIMENTS

Figure 4:
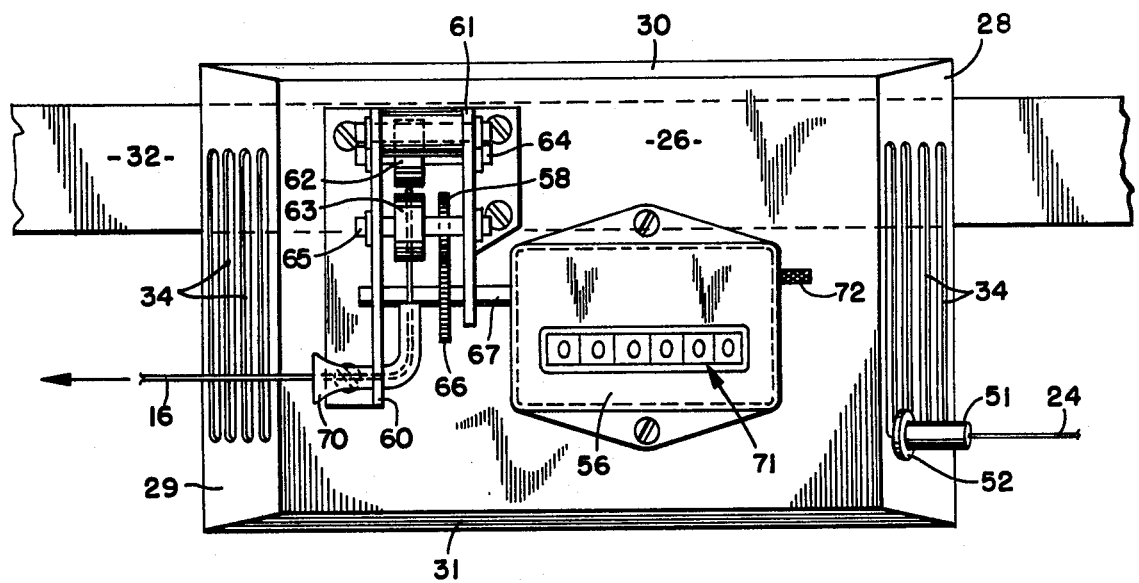
FIG. 4 is a top plan view of the unit of FIG. 2, as seen from the plane of the line 4—4 thereof.

Referring now in detail to the drawings and initially to FIG. 1 thereof, there is illustrated an apparatus, indicated generally at 10, for practicing the method of the present invention for making closely spaced pipe-to-soil potential measurements. A pipe or like structure 11 is shown buried in a soil environment 12 along which a surveyor 14 is traversing carrying the apparatus 10 constructed in accordance with the present invention.

As shown, an elongate electrical conductor or wire 16 is electrically and mechanically connected to the pipe 11 at a reference location, preferably a test lead station 17 which is usually one of several installed at locations along the pipe spaced at one to two mile intervals. The connecting wire is of relatively light weight so that it may be easily carried by the surveyor 14 in contrast to the heavy 300 pound wire reels previously used. The wire is preferably stored in a distance measuring unit 18 from which it is played out behind the surveyor 14 as he traverses the length of the pipeline. A reference electrode 20, such as a conventional copper-copper sulfate half cell, is used for contacting the soil 12 proximate the pipe, and ideally directly over the pipe.

The reference electrode is mounted on the lower end of a cane 21 held by the surveyor for ease in contacting the ground as illustrated in FIG. 1. A meter 22, preferably a high input resistance type voltmeter, is provided on the cane and electrically connected to the half cell 20 to measure the potential difference between the wire 16 connected to the pipe and the reference electrode 20. For convenience in reading the meter, it may be mounted on the top of the cane 21. Electrical connection with one terminal of the meter is provided by a lead wire 23 on the cane to the reference electrode and the other terminal via a lead wire 24 to the distance measuring unit which in turn is connected to the wire 16 as described below. Alternatively, the cane may be hollow and the lead wire 23 inside.

The meter 22, as aforesaid, is preferably an ultra-high resistance input voltmeter of the type designed specifically for such pipe-to-soil potential difference measurements. Accordingly, the resistance of the connecting wire is insignificant, and potentiometric balancing is not required to avoid instrumentation or connecting wire and high soil resistance errors. It is thus possible to have several thousand ohms resistance in the measuring circuit when using such a meter having an input resistance on the order of 11 million ohms. The error would be less than 0.1%. Even using the much more common one meg-ohm meter, the error incurred utilizing 6,000 feet of the enamelled magnet wire of the present invention would be approximately 0.2%. This is well within the accuracy of plus or minus 2% generally accepted for cathodic protection pipe-to-soil potential difference measurements.

Accordingly, it can be seen that the apparatus 10 of the present invention comprises connecting wire 16, distance measuring unit 18, meter 22 and reference electrode 20.

As more clearly shown in FIGS. 2, 3 and 4, the distance measuring unit 18 has a top wall 26 and base 27, front wall 28 and rear wall 29, and inner side wall 30 and outer removable side wall 31. A strap 32 may be secured to the base of the unit by fasteners 33 so that it may easily be carried on the shoulder of the surveyor 14 similar to carrying a large purse as shown in FIG. 1. The walls 28 and 29, may have slots 34 to reduce the weight of the unit as best shown in FIG. 4.

The wire 16 is shown stored on an electrically conductive metal spool 35, which is supported on an electrically conductive upwardly opening U-shape support hook or spindle 36 bolted to the upwardly extending leg 37 of an L-shaped bracket 38 by a suitable fastener 39. The other leg 40 of the bracket is securely mounted on the base 27 of the unit by fasteners 41. A flexible spring strip 42, preferably made of plastic, exerting slight pressure on the wire of spool 35 is provided to prevent backlash and increase electrical contact pressure between the spool and spindle. One end of the strip may be secured to the base 27 and the other contacting the wire wound on the spool intermediate the spool flanges 43 biasing the spool downwardly toward the spindle.

The wire 16 is preferably enamelled copper magnet wire (#32 to #36 A.W.G. is optimum) which may be readily purchased in 2-3 lb. spools of 6,000 to 8,000 feet. As seen in FIG. 5, the spools 35 are mechanically treated by filling an axial notch 44 in the core and flange interface 45 of the spool to expose the interior layer of wire. The notch is then flooded with solder 46 to insure solid electrical contact between the same.

Any excess solder or paint on the interior surface 47 of the core of the spool 35 is filed or sanded off, preferably with fine 400 grit sandpaper. This allows for good electrical contact between the edges of metal spool 35 and the spindle 36 because of the latter's hook or U-shape. The metal spool is free to rotate about the spindle so that the wire may be unwound from the spool while maintaining electrical connection with the spindle. The spindle in turn is connected to one of the terminals of the meter 22 by a lug 49 and lead wire 50 via lead wire 24. A phono plug 51 and socket 52 mounted in the front wall 28 of the unit may be provided for easily electrically disconnecting the meter-reference electrode assembly from the distance measuring unit.

Although applicant has described the preferred arrangement, it is understood that the wire may be electrically connected to the meter by various other methods. For example, contact between the metal spool and spindle may be effected with more sophisticated spring-loaded brushes or the like.

In addition to being of relatively light weight, the connecting wire 16 is sufficiently flexible for driving a distance counter assembly 54 as the wire 16 is played out from the unit 18. The distance counter assembly comprises a transmission assembly 55 and conventional counter mechanism 56 driven thereby secured to the top 26 of the unit for indicating the length of wire played out from the unit. The transmission assembly 55 includes a drive roller 57 and driving gear 58 secured on a shaft 59 journaled upwardly extending plates 60 and 61 mounted on the top 26. The wire as it is drawn through the footage counter is maintained in contact with the roller 57 by guide rollers 62 and 63 similarly mounted on shafts 64 and 65, respectively, between the plates 60 and 61. The guide rollers hold and press the wire against the drive roller 57. The driving gear 58 meshes with a driven gear 66 on shaft 67 which drives the counter mechanism 56. Wire guides 69 and 70, respectively, are provided to properly align the wire entering and leaving the transmission assembly, and facilitate threading. The counter mechanism may be calibrated to indicate on the display 71 thereof the length of wire played out in feet, yards, meters, etc., and is preferably provided with a reset knob 72 for zeroing the meter.

Several extra prepared spools 73 of connecting wire may be carried in the unit on brackets 74 secured to the inner side 30 thereof by fasteners 75. The outer side 31 is preferably removable or hinged providing excess to the interior of the unit for changing spools when the wire on a spool is exhausted. Accordingly, the wire spools may be easily and quickly replaced on the spindle as needed.

It will be appreciated that the distance measuring unit of the present invention may be similar to commercially available distance measuring units which may use string. The lightweight, flexible enamelled magnet wire may be substituted in place of the string normally used in such units. Suitable electric connection modifications must be made as described above.

It can now be seen that a closely spaced survey may be readily conducted in accordance with the present invention by utilizing the above-described apparatus. The distance measuring unit 18 may be easily carried by the surveyor 14 on his shoulder while the voltmeter 22-reference electrode 20 assembly is carried in one hand as shown in FIG. 1. Initially, the surveyor secures one end of the wire 16 to the pipeline 11 at a reference location. This may be easily accomplished by securing the wire to one of the test leads 17 provided at spaced intervals along the pipeline. Accordingly, mechanical and electrical connection is provided simultaneously to the pipeline. The surveyor then traverses the length of the pipeline contacting the ground 12 with the reference electrode 20 at spaced intervals accurately measured by the distance counter assembly 54 as the wire 16 is played out through the same. The surveyor may then record the potential difference and location at each testing point by one of any various methods. This may be efficiently and easily accomplished by transmitting the data to a remote assistant or tape recorder by a radio transmitter 76. Alternatively, the surveyor may carry the tape recorder along with him or simply jot the data down on paper.

When the wire on one spool is exhausted, a new spool may be simply replaced on the spindle 36 as required. Each surveyor preferably carries one or more extra prepared spools and emery cloth for making wire-to-wire connections. The emery cloth is used to quickly remove the enamel after which a simle knot makes the electrical connection.

When the surveyor reaches the next test lead or reference location, the wire is then secured to such test lead and the survey continues as previously described from the new reference location. The wire between the prior test leads or reference locations, being relatively inexpensive, is merely left in place and need never be reeled back for re-use. Such wire is economically disposable and will ultimately disintegrate causing no environmental harm to the tract surveyed. If desired the wire may subsequently be retrieved for scrap.

It will be appreciated that the above survey may be conducted by one person who can traverse the pipeline without encumbrance as the wire is merely played out behind the surveyor with virtually no drag. The surveyor need never retrace his steps. In addition, distance measurement is accomplished at the test location without the need for radio contact or for a man to be positioned at the test lead attachment point or reference location.

Accordingly, it is thus possible using the survey technique of the present invention to survey approximately 2 to 3 times the previous distance covered in a working day using the prior survey technique at about one third to one half the labor cost. This is an increase in efficiency of 400% to 900%.

I, therefore, particularly point out and distinctly claim as my invention:

1. A readily portable apparatus for making relatively closely spaced electrical surveys of sub-surface structures adapted to be manually transported therealong by a single person walking along such structures comprising a portable support, manually held reference electrode means contactible with the surface proximate the structure, a supply of lightweight, small gage, disposable elongate electrically conductive magnet wire means for electrically and mechanically connecting the apparatus with the structure at a reference location thereon, storage means for storing said supply of said wire means on said portable support, meter means electrically connected between said electrode means and said wire means for indicating the potential difference between said reference electrode means and said wire means, and distance measuring means mounted on said portable support and driven by said wire means for measuring the length of said wire means as it is played out from the apparatus as the latter is manually transported along the surface above the structure whereby the structure-to-surface potential difference may be determined by such single person at measured distances along the length of the structure.

2. The apparatus of claim 1 wherein said wire means comprises copper wire.

3. The apparatus of claim 1 wherein said wire means is enamel insulated copper magnet wire.

4. The apparatus of claim 1 wherein said reference electrode means comprises a copper-copper sulfate half cell.

5. The apparatus of claim 1 further comprising a manually held cane and wherein said reference electrode means is secured to the lower end of said cane to be manually placed to contact the surface and said meter means is supported by such single person for facile viewing.

6. The apparatus of claim 1 wherein said wire means is copper wire in a size range of from about No. 32 to about No. 36 A.W.G.

7. The apparatus of claim 1 wherein said storage means comprises an electrically conductive spool means, and further comprising means for supporting said spool means for rotation.

8. The apparatus of claim 7 wherein said means for supporting comprises electrically conductive U-shape spindle means.

9. The apparatus of claim 8 further comprising means for electrically connecting said wire means to said electrically conductive spool means, means for electrically connecting said spool means to said spindle means by mechanical engagement therewith, and means for electrically connecting said spindle means to said meter means to complete an electrical connection between said wire means and said meter means.

10. The apparatus of claim 9 wherein said means for electrically connecting said spool means and said spindle means comprises a soldered notch in the core of said spool means electrically connecting the inner layer of said wire means to said spool means.

11. The apparatus of claim 9, further comprising resilient means for urging said spool means into mechanical and electrical engagement with said spindle to improve electrical connection between said spool means and spindle means and to minimize backlash.

12. The apparatus of claim 9, further comprising a manually held cane and wherein said reference electrode means is secured to the lower end of said cane to be manually placed in contact with the surface, and said meter means is secured to the other end of said cane for facile viewing, said means for electrically connecting said spindle means to said meter means comprises an electrical connector having one portion mounted on said support and another portion electrically coupled to said meter and removably connectable with said one portion.

13. The apparatus of claim 9, said support comprising a housing, said wire means, spool means, and spindle means being mounted in said housing, and said distance measuring means being mounted on said housing to measure wire means played out from said housing.

14. The apparatus of claim 7 further comprising means for carrying additional spool means on said portable support.

15. The apparatus of claim 1, said portable apparatus being of a size and weight to be carried with facility by a person, said support comprising a housing, said storage means comprising a storage reel rotatably mounted in said housing for playing out said wire means as the portable apparatus is manually carried away from a point of connection of said wire means to the structure, and said distance measuring means comprising roller type measuring means for contacting said wire means and rotating as the latter is played out.

16. A method for making relatively closely spaced structure-to-soil potential difference surveys comprising the steps of:
(a) providing a portable supply of a lightweight small gage, disposable, flexible elongate electrical magnet wire conductor,
(b) electrically and mechanically connecting the conductor to the structure at a reference location thereon,
(c) playing out the conductor along the length of the structure through a distance measuring device while transporting the portable supply of the conductor to test locations along the structure,
(d) contacting the soil at such test locations proximate the structure with reference electrode,
(e) measuring and observing the potential difference at each such test location between the reference electrode and the conductor,
(f) recording the measured potential difference and distance indicated by the distance measuring device, and
(g) leaving the conductor when the survey is completed for disposal.

17. The method of claim 16 wherein such test locations are at closely spaced regular intervals along the structure.

18. The method of claim 16 further comprising the step of recording both such distance and potential measurements at such test location.

19. The method of claim 18 wherein both the distance and potential measurements at such test location are transmitted to a remote location for recording of the same.

20. The method of claim 16 wherein the conductor is stored on an electrically conductive spool, the method further comprising the step of mechanically treating the spool by filing a notch in the inner core to expose the interior layer of the electrical conductor and flooding such notch with solder to assure good electrical contact between the interior layer of the electrical conductor and spool at the notch.

21. The method of claim 16 further comprising the step of splicing a second lightweight elongate electrical conductor to the end of the first lightweight elongate electrical conductor when the latter is exhausted to maintain continuity of electrical connection with the structure.

22. The method of claim 16 wherein the step of measuring potential difference comprises measuring the same by a high resistance meter.

23. The method of claim 22 wherein such structure is a buried pipeline and the step of transporting comprises manually carrying such supply, reference electrode and meter by a single person walking along the pipeline right of way. f 24. The method of claim 23 further comprising the step of mounting the reference electrode and meter on a cane and wherein the step of transporting comprises manually carrying the cane in one hand of the person.

* * * * *